US00PP25739P3

(12) United States Plant Patent
Miller et al.

(10) Patent No.: US PP25,739 P3
(45) Date of Patent: Jul. 21, 2015

(54) ***LAVANDULA* PLANT NAMED 'VOODOO'**

(50) Latin Name: *Lavandula stoechas*
Varietal Denomination: Voodoo

(71) Applicants: Luen Miller, Santa Cruz, CA (US); Manuel Morales, Royaloaks, CA (US)

(72) Inventors: Luen Miller, Santa Cruz, CA (US); Manuel Morales, Royaloaks, CA (US)

( * ) Notice: Subject to any disclaimer, the term of this patent is extended or adjusted under 35 U.S.C. 154(b) by 42 days.

(21) Appl. No.: 13/986,394

(22) Filed: Apr. 26, 2013

(65) Prior Publication Data

US 2014/0325724 P1 Oct. 30, 2014

(51) Int. Cl.
*A01H 5/02* (2006.01)
*A01H 5/00* (2006.01)

(52) U.S. Cl.
USPC ..... Plt./445
CPC ... *A01H 5/02* (2013.01); *A01H 5/00* (2013.01)

(58) Field of Classification Search
USPC ..... Plt./445
See application file for complete search history.

*Primary Examiner* — June Hwu
*Assistant Examiner* — Keith Robinson
(74) *Attorney, Agent, or Firm* — Cassandra Bright

(57) ABSTRACT

A new and distinct *Lavandula* cultivar named 'Voodoo' is disclosed, characterized by a long, dark purple terminal bracts with a broad angle of attachment. The new variety can also be characterized its round plant shape and long peduncle length. The new variety is a *Lavandula*, normally produced as an outdoor garden or container plant.

2 Drawing Sheets

Figure 1:
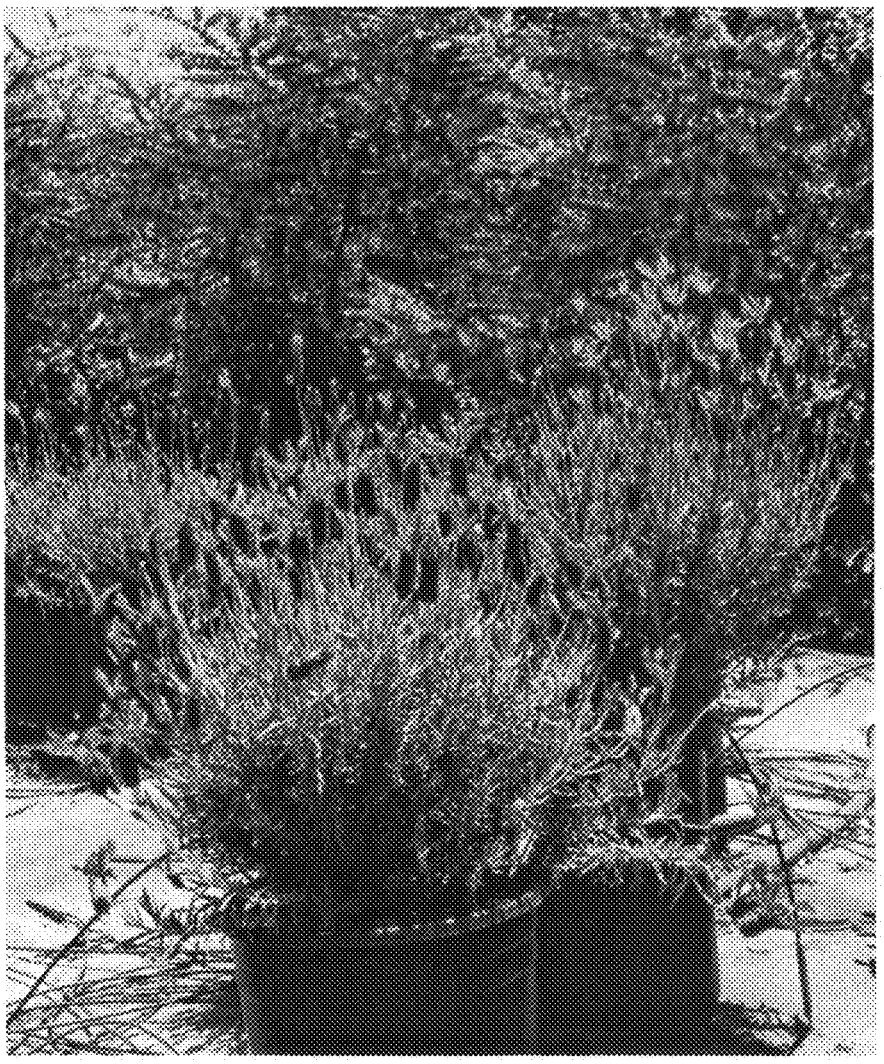

Latin name of the genus and species: *Lavandula stoechas*.
Variety denomination: 'Voodoo'.

BACKGROUND OF THE INVENTION

The new *Lavandula* cultivar is a product of a chance discovery by the inventors, Luen Miller and Manuel Morales. The new variety was discovered at a commercial nursery belonging to the inventors, in Watsonville, Calif.

The new variety was selected during Spring of 2011 as a seedling of undetermined parentage. The seedling was discovered among plantings of *Lavandula stoechas* 'Dedication', unpatented and *Lavandula stoechas* 'Otto Quast', unpatented. The inventors presume these two varieties are the parent varieties.

Asexual reproduction of the new cultivar was first performed by vegetative cuttings Dec. 9, 2011 at the same commercial nursery in Watsonville, Calif. Subsequent propagation has shown that the unique features of this cultivar are stable and reproduced true to type through successive generations.

SUMMARY OF THE INVENTION

The cultivar 'Voodoo' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Voodoo'. These characteristics in combination distinguish 'Voodoo' as a new and distinct *Lavandula* cultivar:

1. Dark purple infertile bract coloration.
2. Long length of infertile bracts.
3. Round plant form.
4. Wide angle of attachment and attitude of infertile bracts.

5. Long peduncle length.
6. Straight peduncles.
7. Strong, durable flowers.

Plants of the new cultivar 'Voodoo' are similar to plants of the presumed parent, *Lavandula stoechas* 'Dedication' in most horticultural characteristics, however, plants of the new cultivar 'Voodoo' produce flowers of a darker purple. Flowers of 'Dedication' are colored close to Purple-Violet N81D. Additionally, the flowers last longer and produce infertile bracts that have a wider angle of attachment and attitude than 'Dedication'.

Plants of the new cultivar 'Voodoo' are similar to plants of the presumed parent; *Lavandula stoechas* 'Otto Quast' in most horticultural characteristics, however, plants of the new cultivar 'Voodoo' produce flowers of a different color. Flowers of 'Otto Quast' are in the range of Violet 83A, whereas flowers, of 'Voodoo' are near Violet-Blue N89B. Terminal bracts of 'Otto Quast' are near Purple-Violet N82C; bracts of 'Voodoo' are near Violet 83B, with darker veins near Violet-Blue N92A . Additionally, plants of the new variety produce infertile bracts that have a wider angle of attachment and attitude than 'Otto Quast'.

COMMERCIAL COMPARISON

Plants of the new cultivar 'Voodoo' are comparable to the variety *Lavandula* 'Larkman Bee', U.S. Plant Pat. No. 20,480. The two *Lavandula* varieties are similar in most horticultural characteristics; however, the new variety 'Voodoo' differs in producing longer infertile bracts, longer peduncles and an overall longer flower than the comparator. Additionally 'Voodoo' produces a plant of stronger vigor and larger mature size than the comparator.

Plants of the new cultivar 'Voodoo' can also be compared to the commercial variety *Lavandula* 'Larkman Hazel' U.S. Plant Pat. No. 20,894. These varieties are similar in most horticultural characteristics however, the new variety 'Voodoo' differs in producing longer infertile bracts, longer peduncles and an overall longer flower than the comparator. Additionally 'Voodoo' produces a plant of stronger vigor and larger mature size than the comparator.

BRIEF DESCRIPTION OF THE PHOTOGRAPHS

The accompanying photograph in FIG. 1 illustrates in full color a typical plant of 'Voodoo' grown outdoors in Watsonville, Calif. The prominent plant in the foreground is 'Voodoo'. The plant in the background, with a less regular, round shape is *Lavendula* 'Dedication'. Age of the plants photographed is approximately 50 weeks from a rooted cutting.

Figure 2:
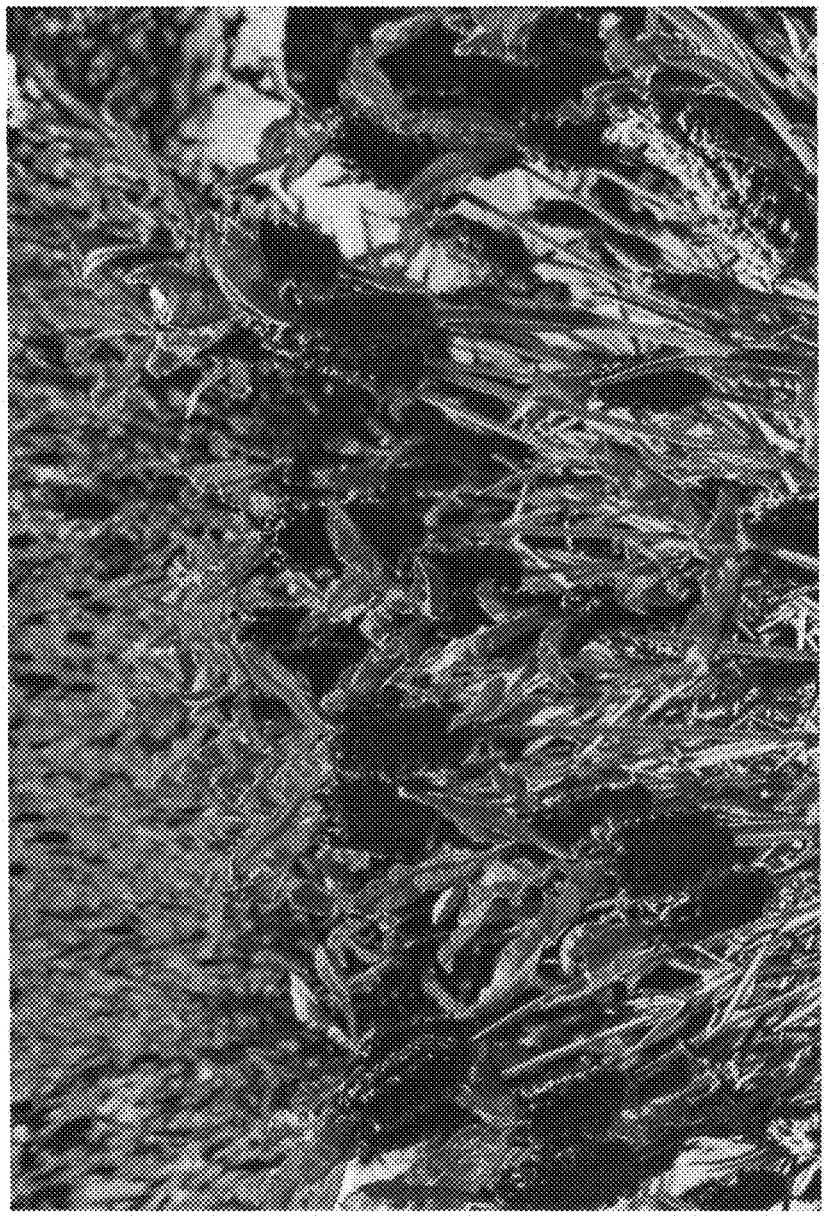

FIG. 2 illustrates a close up of the flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Voodoo' plants grown outdoors during, Fall, Winter and Spring in Watsonville, Calif. The growing temperature ranged from 10° C. to 35° C. during the day and from 5° C. to 25° C. during the night. General light conditions are bright, normal sunlight. Measurements and numerical values represent averages of typical plant types.

Botanical classification: *Lavandula stoechas* 'Voodoo'.

PROPAGATION

Time to initiate roots: About 10 to 14 days at approximately 21° C.

Time to produce a rooted cutting: About 25 to 35 days at 21° C.

PLANT

Age of plant described: Approximately 50 weeks from a rooted cutting.

Plant spread: Approximately 60 cm.

Plant height: Approximately 50 cm, to top of flowering plane. Approximately 30 cm to top of foliar plane.

Growth rate: Moderate to fast.

Plant vigor: Moderate to robust.

Length of primary lateral branches: Approximately 16 cm.

Diameter of lateral branches: Approximately 0.35 cm.

Quantity of lateral branches: About 50.

Plant habit: Moderately dense, rounded ball shape. Plants typically pinched once, encouraging lateral branching. No basal branching.

Stem:

*Juvenile color*.—Near Yellow-Green group RHS 145B.

*Mature color*.—Near Yellow-Green 147D.

*Texture/pubescence*.—Densely pubescent.

*Shape*.—Round in cross-section.

*Strength*.—Very strong and flexible.

Internode length: Average 1.0 cm.

PROPAGATION and ROOTS

Time to initiate roots: About 10-14 days at approximately 21° C.

Time to produce a rooted cutting: About 25-35 days at 21° C.

*Root description*.—Fine, fibrous, developing a woody texture with age. Roots colored near RHS Greyed-Orange 175A, 177A.

FOLIAGE

Leaf:

*Arrangement*.—Opposite.

*Leaf type*.—Simple.

*Quantity*.—Average 16 fully expanded per main branch and 20 juvenile leaves.

*Average length*.—Average 3.4 cm. (mature foliage).

*Average width*.—Average 0.4 cm. (mature foliage).

*Shape of blade*.—Lanceolate.

*Apex*.—Acute.

*Base*.—Truncate.

*Attachment*.—Sessile.

*Margin*.—Entire.

*Texture of all surfaces*.—Pubescent.

*Leaf fragrance*.—Very strong Lavender scent.

*Color*.—Young foliage upper side: Near Yellow-Green 147B. Young foliage under side: Near Green RHS 137D. Mature foliage upper side: Near Green RHS 137B. Mature foliage under side: Near Green RHS 137A.

*Venation*.—Type: Reticulate. Venation color upper side: Near Yellow-Green 144A, only main vein distinguishable from foliage color. Venation color under side: Near Yellow-Green 145B.

*Petiole*.—Absent.

FLOWER

Bloom period: Main flush late winter to late spring. Lesser quantities of flowers produced throughout Summer and Fall.

Bud:

*Length*.—Approximately 0.8 cm.

*Diameter*.—Approximately 0.4 cm.

*Shape*.—Ovate.

*Color*.—Near RHS Near Violet-Blue N89B.

*Rate of opening*.—Varies with climactic conditions; Approximately 5 to 10 days from colored bud to open flower.

Inflorescence:

*Form*.—Small single flower in verticillasters arranged in spikes. Most commonly 8 rows of flowers. Infrequently 6 or 10 rows. Flowers have small bracts, and large showy terminal bracts. One flower spike per lateral stem. Number of individual flowers per spike: Average 144. Fragrance: Very strong lavender scent. Flower lastingness: Individual flowers last approximately 2 to 3 weeks, inflorescence remain ornamental for approximately 4 to 6 weeks. Self-cleaning. Corolla shape: Salverform. Petal Number: 5. Petals Fused or Unfused: Fused at base. Petal apex: Obtuse. Petal base: Fused. Petal Shape: Top 2 lobes obovate, lower 3 lobes ovate. Petal Margin: Entire. Petal Surfaces: Glabrous. Length: Approximately 0.8 cm. (corolla tube). Diameter: Approximately 0.3 cm.

*Inflorescence size, excluding terminal bracts*.—Length: Approximately 5.5 cm. Width: Approximately 1.8 cm. Shape: Cylindrical. Coloration of individual flowers, excluding terminal bracts: Immature: Near Violet-Blue N89B. Mature: Near Violet-Blue N89B, base N155D. Fading: Near Violet-Blue N92B, base N155D. Calyx Width: 0.2 cm. Calyx Length: 0.95 cm. Calyx Shape: Flattened tube. Calyx color: RHS Yellow-Green 144C. Bract shape: Elliptic. Bract apex: Acute with a cusp. Bract Color: Near Yellow-Green 144C, cusp colored Greyed-Purple 187A.

Terminal bracts (sterile): Quantity: 4 large and 1 or 2 smaller per inflorescence.

*Large bracts*.—Attitude and angle of attachment: At least 2 of the large bracts are attached at an obtuse angle, near 75°. Terminal bracts and an upward and outwardly angled attitude. Length: Approximately 3.5 to 4.5 cm. Width: Approximately 1.0 cm. Form: Petaloid. Margin: Entire and undulating. Surface: Smooth. Appearance: Matte. Shape: Oblanceolate. Apex: Acute. Base: Attenuate. Vein Pattern: Reticulate. Duration on Plant: Approximately 12 weeks, with good color. Persistent. Color: Upper side of immature bract: Near RHS Violet 83C, base lighter, 83D. Veins darker, near Violet-Blue N92A. Under side of immature bract: Near RHS Violet 83B, base lighter, 83C. Veins darker, near Violet-Blue N92A. Upper side of mature bract: Near RHS Violet 83B. Under side of mature bract: Near RHS Violet 83A. Bract color fading to: Near RHS Purple 79B.

*Small bracts*.—Quantity: typically 1 or 2. Length: Approximately 2.0 to 3.0 cm. Width: Approximately 0.8 cm, unfolded. Apex: Shallow bi-lobe. Margin: Entire, undulating. Base: Attemiate. Aspect: Undulating and folded inward at the mid-vein. Duration on Plant: Approximately 12 weeks. Persistent. Color: Upper side of immature bract: Near RHS Violet 83C, base lighter, 83D. Veins darker, near Violet-Blue N92A. Under side of immature bract: Near RHS Violet 83B, base lighter, 83C. Veins darker, near Violet-Blue N92A. Upper side of mature bract: Near RHS Violet 83B. Under side of mature bract: Near RHS Violet 83A. Bract color fading to: Near RHS Purple 79B.

Peduncle:

*Peduncle length*.—Average range approximately 9 to 11 cm.

*Peduncle diameter*.—Approximately 0.4 cm.

*Aspect*.—Very straight.

*Color*.—Near RHS Green 138C.

*Texture*.—Densely pubescent and ridged.

REPRODUCTIVE ORGANS

Androecium:

*Stamens*.—4.

*Anther shape*.—Linear.

*Anther length*.—Approximately 0.05 cm.

*Anther color*.—Near RHS White N155A.

*Pollen quantity*.—Pollen production not observed.

Pistil:

*Number*.—1.

*Length*.—Approximately 0.4 cm.

*Style*.—Length: Approximately 0.3 cm. Color: Near RHS White N155A.

*Stigma*.—Length: Approximately 0.05 cm. Shape: Linear. Color: Near RHS Violet-Blue N92B. Ovary: Minute and immeasurable.

OTHER CHARACTERISTICS

Seeds and fruits: Seed production not observed to date.

Disease/pest resistance: Neither resistance nor susceptibility to the normal diseases and pests of *Lavandula stoechas*. has been observed.

Drought tolerance and cold tolerance: Hardy perennial. Tolerates high temperature to at least 32° C. Tolerates low temperatures to −12° C. While specific drought tolerance has not been observed, once plants are established very little water is necessary to maintain plants.

Fruit/seed production: Fruit and seed production not observed.

What is claimed is:

1. A new and distinct cultivar of *Lavandula* plant named 'Voodoo' as herein illustrated and described.

* * * * *